US010898085B2

(12) United States Patent
De Groot et al.

(10) Patent No.: US 10,898,085 B2
(45) Date of Patent: Jan. 26, 2021

(54) PULSE WAVE VELOCITY DETERMINATION, FOR EXAMPLE FOR BLOOD PRESSURE MONITORING

(71) Applicant: KONINKLIJKE PHILIPS N.V., Eindhoven (NL)

(72) Inventors: Koen Theo Johan De Groot, Sevenum (NL); Mustafa Ghassan Radha, Veldhoven (NL); Jozef Hubertus Gelissen, Herten (NL); Reinder Haakma, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/467,732

(22) PCT Filed: Dec. 6, 2017

(86) PCT No.: PCT/EP2017/081618
§ 371 (c)(1),
(2) Date: Jun. 7, 2019

(87) PCT Pub. No.: WO2018/104359
PCT Pub. Date: Jun. 14, 2018

(65) Prior Publication Data
US 2019/0365256 A1    Dec. 5, 2019

(30) Foreign Application Priority Data
Dec. 9, 2016   (EP) ..................................... 16203145

(51) Int. Cl.
*A61B 5/021*     (2006.01)
*A61B 5/02*      (2006.01)
(Continued)

(52) U.S. Cl.
CPC ...... *A61B 5/02125* (2013.01); *A61B 5/02007* (2013.01); *A61B 5/0816* (2013.01);
(Continued)

(58) Field of Classification Search
None
See application file for complete search history.

(56) References Cited

U.S. PATENT DOCUMENTS 4,827,763 A * 5/1989 Bourland ............... A61B 5/113
                                                      361/283.1
6,511,436 B1 * 1/2003 Asmar ................... A61B 5/021
                                                      600/481
(Continued)

FOREIGN PATENT DOCUMENTS

CN     102197996 A     9/2011
CN     104825144 A     8/2015
(Continued)

OTHER PUBLICATIONS

International Search Report and Written Opinion, International Application No. PCT/EP2017/081618, dated Mar. 26, 2019.
(Continued)

*Primary Examiner* — Michael R Bloch

(57) ABSTRACT

A pressure distribution profile of a subject lying on a mat is used to derive a measure of pulse wave velocity. Beat locations are identified where beat pressure signals are identified, and pulse timing information is obtained from the beat locations. By determining a subject posture, the beat locations are mapped to anatomical body locations and arterial path length information is obtained for the anatomical body locations. A pulse wave velocity is then estimated from the pulse timing information and arterial path lengths. This method enables measuring the pulse wave velocity during sleep in a comfortable, easy and unconstrained manner. This is accomplished by analyzing signals from a
(Continued)

pressure sensitive surface for example on top of a bed mattress or by embedding a pressure sensitive layer in the mattress.

15 Claims, 5 Drawing Sheets

(51) Int. Cl.
A61B 5/08 (2006.01)
A61B 5/11 (2006.01)
A61B 5/00 (2006.01)

(52) U.S. Cl.
CPC ............ *A61B 5/1102* (2013.01); *A61B 5/1113* (2013.01); *A61B 5/6892* (2013.01); *A61B 2562/0219* (2013.01)

(56) References Cited

U.S. PATENT DOCUMENTS

| | | | |
|---|---|---|---|
| 2003/0036685 A1* | 2/2003 | Goodman | G06F 19/3418 600/300 |
| 2004/0010202 A1* | 1/2004 | Nakatani | A61B 5/0816 600/529 |
| 2005/0038347 A1* | 2/2005 | Suzuki | A61B 5/02444 600/500 |
| 2005/0124864 A1* | 6/2005 | Mack | A61B 5/024 600/300 |
| 2006/0173273 A1 | 8/2006 | Boese et al. | |
| 2011/0112442 A1* | 5/2011 | Meger | A61B 5/4094 600/595 |
| 2012/0184862 A1* | 7/2012 | Foo | A61B 5/113 600/508 |
| 2012/0323501 A1* | 12/2012 | Sarrafzadeh | G01L 1/205 702/41 |
| 2014/0155774 A1* | 6/2014 | Sarrafzadeh | A61B 5/7282 600/529 |
| 2015/0045630 A1* | 2/2015 | Poliakine-Baruchi | A61B 5/7475 600/301 |
| 2015/0087894 A1* | 3/2015 | Rink | A61M 21/02 600/28 |
| 2015/0196209 A1 | 7/2015 | Morris et al. | |
| 2015/0351694 A1 | 12/2015 | Shimizu et al. | |
| 2016/0089042 A1 | 3/2016 | Saponas et al. | |
| 2016/0174852 A1* | 6/2016 | He | A61B 5/0285 600/301 |
| 2016/0262695 A1 | 9/2016 | Zhang et al. | |
| 2016/0367171 A1* | 12/2016 | Shimizu | A61B 5/107 |

FOREIGN PATENT DOCUMENTS

| | | |
|---|---|---|
| EP | 2862507 A1 | 4/2015 |
| JP | 4117398 | 7/2008 |
| JP | 2016150065 A | 8/2016 |
| WO | 2003082111 A1 | 10/2003 |
| WO | 2015107269 A1 | 7/2015 |
| WO | 2015193551 A1 | 12/2015 |

OTHER PUBLICATIONS

Yilmaz, T. et al., "Detecting Vital Signs with Wearable Wireless Sensors", Department of Electronic Engineering, Queen Mary University of London, 2010.
Markets and Markets, "Vital Signs Monitoring Market—Landscape Analysis of Blood Pressure Monitoring Devices, Pulse Oximeters and Temperature Monitoring Devices—Forecasts up to 2018", https://www.marketsandmarkets.com/Market-Reports/vital-signs-monitoring-devices-market-1154.html, 2013, Accessed Jun. 2019.
"High Blood Pressure Facts", Centers for Disease Control and Prevention, https://www.cdc.gov/bloodpressure/facts.htm, Nov. 2016.
McGhee, B. et al., "Monitoring arterial blood pressure: what you may not know", Crit Care Nurse. Apr. 2002;22(2):60-4, 66-70.
Alpert et al, Oscillometric blood pressure: A review for clinicians, Am. Soc. Hypertension, 2014.
Elgendi, On the analysis of fingertip photoplethysmogram signals, Current Cardiology Reviews, 2012.
Mukkamala et al, Towards ubiquitous blood pressure monitoring via pulse transit time: Theory and practice, IEEE transactions on biomedical engineering, 2015.
Proença et al, Is Pulse Transit Time a good indicator of Blood Pressure changes during short physical exercise in a young population?, IEEE conference EMBS 2010.
Monte-Moreno, E., "Non-invasive estimate of blood glucose and blood pressure from a photoplethysmograph by means of machine learning techniques", Artificial Intelligence in Medicine, 2011.
https://www.heart.org/en/health-topics/high-blood-pressure/understanding-blood-pressure-readings, American Heart Association, Inc., 2019.
https://www.tekscan.com/, Tekscan, Inc., 2019.

* cited by examiner

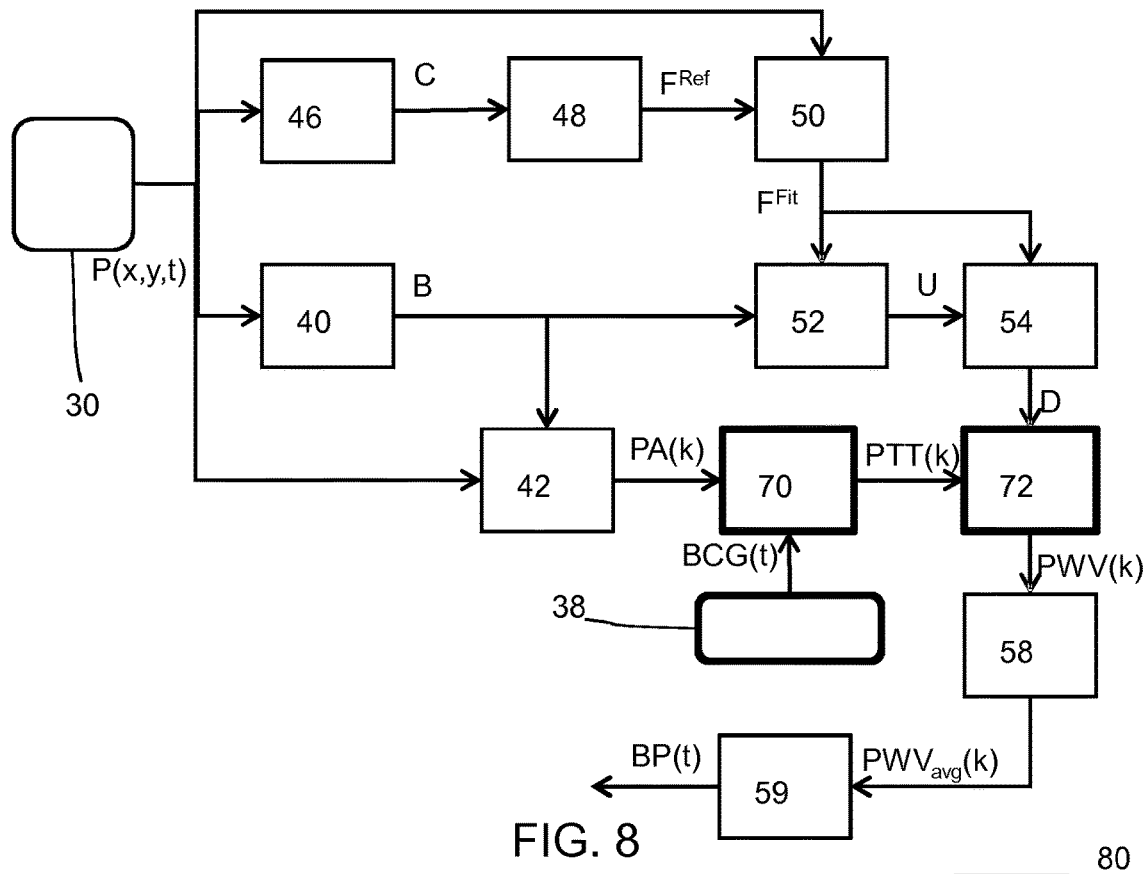
FIG. 8
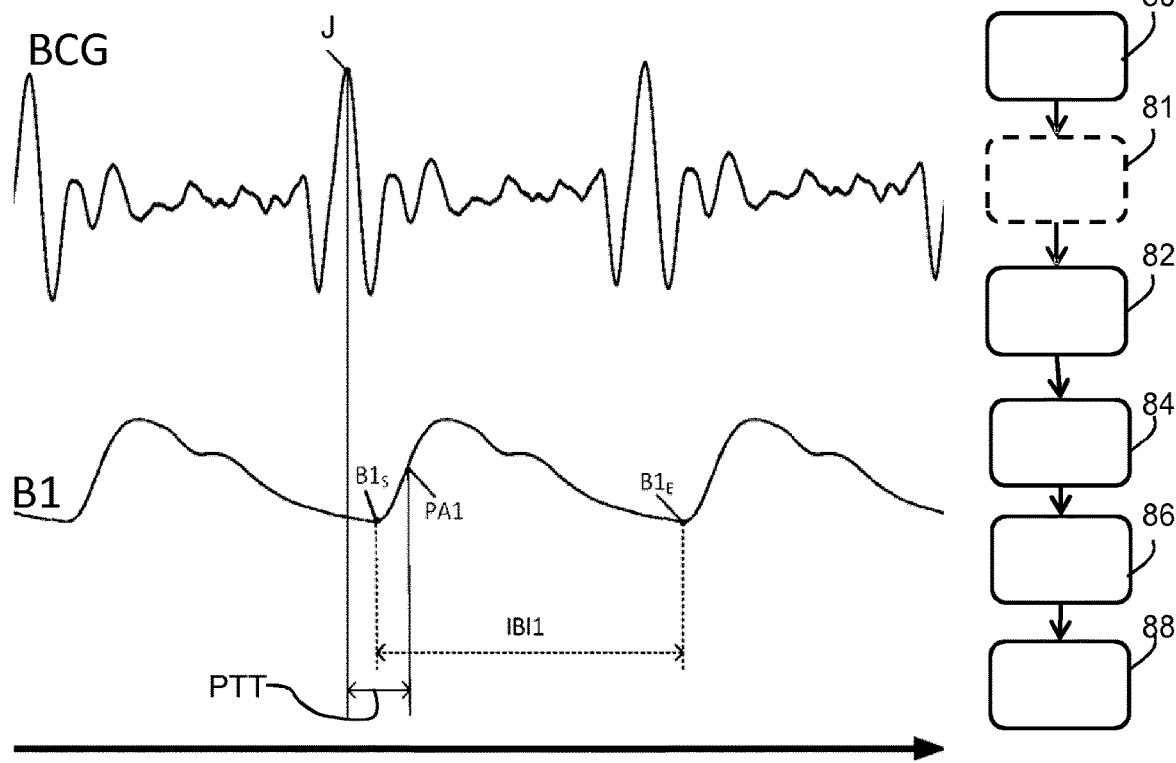
FIG. 9
FIG. 10

PULSE WAVE VELOCITY DETERMINATION, FOR EXAMPLE FOR BLOOD PRESSURE MONITORING

CROSS-REFERENCE TO PRIOR APPLICATIONS

This application is the U.S. National Phase application under 35 U.S.C. § 371 of International Application Serial No. PCT/EP2017/081618, filed on 12 Jun. 2017, which claims the benefit of European Application Serial No. 16203145.4, filed on 12 Sep. 2016. These applications are hereby incorporated by reference herein.

FIELD OF THE INVENTION

This invention relates to the determination of pulse wave velocity, for example for blood pressure monitoring, and in particular during sleep.

BACKGROUND OF THE INVENTION

There is increasing demand for unobtrusive health sensing systems. In particular, there is a shift from conventional hospital treatment towards unobtrusive vital signs sensor technologies, centered around the individual, to provide better information about the subject's general health.

Such vital signs monitor systems help to reduce treatment costs by disease prevention and enhance the quality of life. They may provide improved physiological data for physicians to analyze when attempting to diagnose a subject's general health condition. Vital signs monitoring typically includes monitoring one or more of the following physical parameters: heart rate, blood pressure, respiratory rate and core body temperature.

In the US about 30% of the adult population has a high blood pressure. Only about 52% of this population have their condition under control. Hypertension is a common health problem which has no obvious symptoms and may ultimately cause death, and is therefore often referred to as the "silent killer". Blood pressure generally rises with aging and the risk of becoming hypertensive in later life is considerable. About 66% of the people in age group 65-74 have a high blood pressure. Persistent hypertension is one of the key risk factors for strokes, heart failure and increased mortality.

The condition of the hypertensive patients can be improved by lifestyle changes, healthy dietary choices and medication. Particularly for high risk patients, continuous 24 hour blood pressure monitoring is very important and there is obviously a desire for systems which do not impede ordinary daily life activities.

Blood pressure is usually measured as two readings: systolic and diastolic pressure. Systolic pressure occurs in the arteries during the maximal contraction of the left ventricle of the heart. Diastolic pressure refers to the pressure in arteries when the heart muscle is resting between beats and refilling with blood. Normal blood pressure is considered to be 120/80 mmHg. A person is considered to be hypertensive when the blood pressure is above 140/90 mmHg, and two stages of hypertension may be defined for increasing blood pressure levels, with hypertensive crisis defined when blood pressure reaches 180/110 mmHg. Note that for conversion of these values to metric equivalents, 760.0 mmHg is equal to 101.325 kPa. There are two main classes of methods to monitor blood pressure.

For invasive direct blood pressure monitoring, the gold standard is by catheterization. A strain gauge in fluid is placed in direct contact with blood at any artery site. This method is only used when accurate continuous blood pressure monitoring is required in dynamic (clinical) circumstances. It is most commonly used in intensive care medicine and anesthesia to monitor blood pressure in real time.

For non-invasive indirect blood pressure monitoring, oscillometry is a popular automatic method to measure blood pressure. The method uses a cuff with integrated pressure sensor. However, for blood pressure monitoring during sleep it is regarded as an uncomfortable method as the cuff usually inflates and deflates at regular time intervals to measure the subject's blood pressure. This often has a huge negative impact on the sleep quality.

Other non-invasive methods to estimate blood pressure are based on pulse wave velocity (PWV). This technique is based on the fact that the velocity of the pressure pulse traveling through an artery is related to blood pressure. The PWV is derived from the pulse transit time (PTT). Usually the pulse transit time is estimated by: (i) sampling and filtering the pressure pulse waveforms, (ii) detecting beats in the waveforms, (iii) detecting features within the beats that serve as reference point (pulse arrival moment) and (iv) calculating the PTT as the time delay between the features.

PWV is obtained by: PWV=D/PTT, where D refers to the pulse travel distance. The PWV can be translated to a blood pressure estimate by means of a calibration step. Often the Moens-Korteweg equation is applied which describes the relationship between blood pressure and PWV.

If the pulse travel distance D is stable during a measurement, the blood pressure can be directly inferred from PTT by means of a calibration function.

Other methods to measure blood pressure include techniques based on auscultation, tonometry, ultrasonic measurements, and pulse wave morphology.

There remains a need for a non-invasive and comfortable blood pressure monitoring system.

SUMMARY OF THE INVENTION

The invention is defined by the claims.

According to examples in accordance with an aspect of the invention, there is provided a method of analyzing a pressure distribution profile of a subject lying on a mat over time to derive a measure of pulse wave velocity of the subject, wherein the method comprises:
  identifying beat locations where beat pressure signals are identified;
  obtaining pulse timing information from the beat locations;
  determining a subject posture and map the beat locations to anatomical body locations;
  determining an arterial path length for the anatomical body locations; and
  estimating a pulse wave velocity from the pulse timing information and arterial path lengths.

This method enables measuring the pulse wave velocity during sleep in a comfortable, easy and unconstrained manner. This is accomplished by analyzing signals from a pressure sensitive surface for example on top of a bed mattress or by embedding a pressure sensitive layer in the mattress.

While a subject is lying horizontally on the pressure sensitive surface, a spatiotemporal modulation of pressure is recorded, which results from a change in pressure load caused by the pulsating blood flow through a near-surface artery that is in close proximity to sensing surface. In this way, there is no need to wear any on-body sensors such as PPG, ECG or acceleration sensors in order to implement the method. There is no need for ECG sensing technology, and this means that the procedure to estimate pulse wave velocity from pulse transit times is not affected by a positive expiratory pressure (PEP) if the subject is using a PEP device.

The method involves identifying beat locations, for example by spatiotemporal analysis of pressure modulations that characterize variations in the blood volume pulse. The pressure-time signal at those beat locations is used to derive timing information which relates to the arrival of the pulse at that location. The location is also mapped to a physical body position so that an arterial path length estimate can be made. A pulse wave velocity can then be derived.

In this way, the method provides automatic recognition of the body position where a pulse has been detected, and then uses timing information as well as distance information to derive a pulse wave velocity.

The method may comprise obtaining pulse timing information from the beat locations by analyzing the pressure signals to determine a start and end of the cardiac cycle and pulse arrival moment at that location within a given cardiac cycle.

The pulse arrival moment is for example obtained based on detecting the pulse onset during the systolic phase, for example by detecting the moment when a pressure gradient reaches its maximum during the systolic phase of the cardiac cycle.

A pulse arrival moment is for example obtained for each beat location and for each cardiac cycle.

In a first approach, obtaining pulse timing information comprises obtaining a set of pulse delay estimates based on the difference between the pulse arrival moments for a set of pairs of beat locations. This makes use of relative timing information between pairs of locations where a pulse is detected.

In a second approach, the method further comprises receiving a body motion signal indicative of the heart's activity in respect of the subject, wherein obtaining pulse timing information comprises obtaining a set of pulse transit times for the set of beat locations based on the pulse arrival moments for the set of beat locations and the body motion signal. The body motion signal is for example able to indicate when the blood ejects from the heart and enters the aorta. The motion signal is for example a ballistocardiogram.

The method in this case may comprise detecting a peak in the body motion signal and determining a time difference between the timing of the peak and the pulse arrival time for each beat location.

This approach is based on obtaining pulse transit times, which are then converted to pulse wave velocity values.

In both approaches, obtaining a subject posture may comprise matching the measured pressure distribution to a set of predefined reference human form models. The models for example provide different lying down postures and enable the locations of the head, heart and limbs to be mapped to the pressure distribution pattern.

Determining an arterial path length for the anatomical body locations then may comprise mapping the beat location to the matched human form model.

An average pulse wave velocity may be obtained for a processed set of cardiac cycles. A blood pressure measure may then be obtained from the (average) pulse wave velocity. Other measures may also be inferred from the PWV, such as a measure of arterial stiffness, and breathing rate.

The method may be implemented in software.

The invention also provides a monitoring system comprising:

a pressure sensitive mat for providing a pressure distribution profile of a subject lying on the mat over time; and a controller for analyzing the pressure distribution to derive a measure of pulse wave velocity of the subject, wherein the controller is adapted to perform the method as defined above.

The pressure sensitive mat (also referred to as pressure sensitive surface) for example contains pressure sensitive elements that are arranged in a dense 2D grid producing a pressure distribution sequence.

An acceleration sensor may be provided for obtaining a body motion signal, for example in the form of a ballistocardiogram.

The pressure sensitive mat may be adapted to be arranged on top of a bed mattress or, alternative, be configured as a layer embedded in the mattress.

The invention also provides a mattress, such as for example a bed mattress, comprising a monitoring system as defined above.

BRIEF DESCRIPTION OF THE DRAWINGS

Examples of the invention will now be described in detail with reference to the accompanying drawings, in which:

FIG. 8 shows a block diagram of the processing units used within the system of FIG. 7;

FIG. 9 shows how the pulse transit time calculations may be performed; and

FIG. 10 shows a method of analyzing a pressure distribution profile.

DETAILED DESCRIPTION OF THE EMBODIMENTS

The invention provides a method and system in which a pressure distribution profile of a subject lying on a mat is used derive a measure of pulse wave velocity. Beat locations are identified where beat pressure signals are identified, and pulse timing information is obtained from the beat locations. By determining a subject posture, the beat locations are mapped to anatomical body locations and arterial path length information is obtained for the anatomical body locations. A pulse wave velocity is then estimated from the pulse timing information and arterial path lengths. This method enables a comfortable, easy and unconstrained method to measure the pulse wave velocity during sleep. This is accomplished by analyzing signals from a pressure sensitive surface for example on top of a bed mattress or by embedding a pressure sensitive layer in the mattress.

The invention provides a system and method which makes use of the concepts of pulse wave velocity (PWV) and pulse transit time (PTT).

It is known that PTT and PWV can be used as a predictor of blood pressure. The information obtained by these measures is discussed below.

PTT is defined as the propagation time of a blood pulse wave to travel a certain distance in an arterial segment. In practice often the combination of electrocardiography (ECG) and photoplethysmography (PPG) is employed to measure pulse propagation time because of the convenient way to monitor the ECG R-wave and pulse arrival moment in a distal artery with PPG. However, the combination of ECG and PPG measures pulse arrival time (PAT), which is equal to the sum of PTT and the pre-ejection period (PEP).

The PEP is not related to propagation of the blood pulse wave through the arteries. Indeed, if two PPG sensors are positioned on the same arterial branch at distinct locations, one could determine the difference in pulse transit time which is also referred to as pulse delay (PD).

Alternatively, two pulse arrival moments may be measured for every heart beat in two distinct arterial branches. This also yields a pulse delay.

Figure 1:
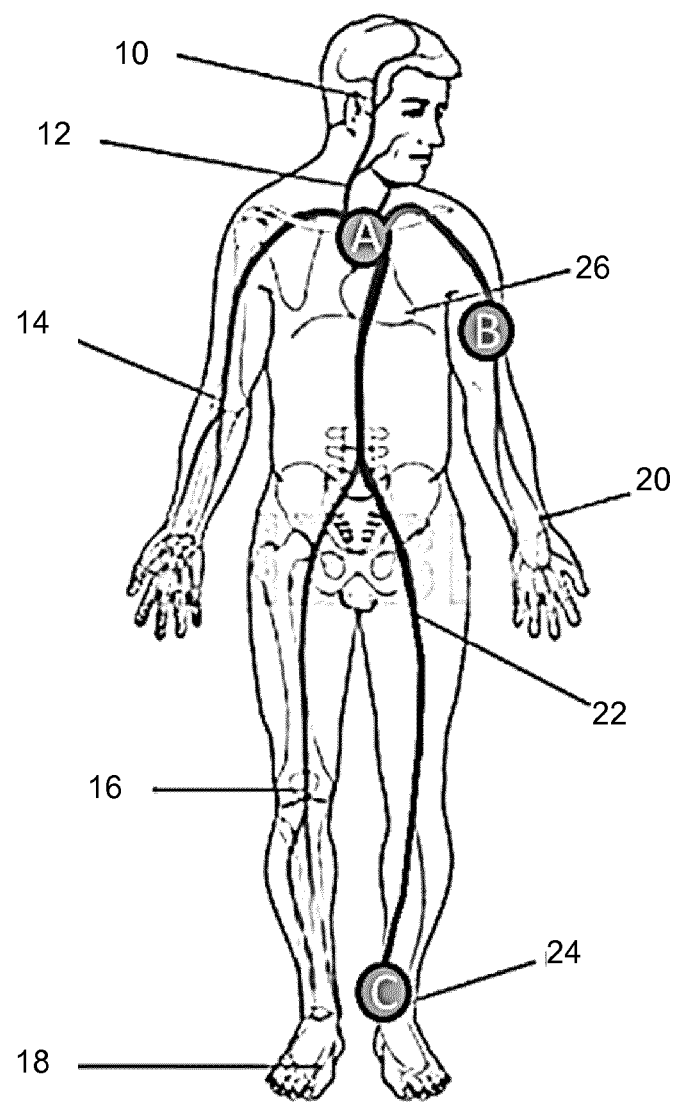
FIG. 1 shows how pulse delay (PD) and pulse wave velocity (PWV) can be determined.

FIG. 1 shows how pulse delay (PD) and pulse wave velocity (PWV) can be determined. FIG. 1 shows a subject with the location of their temporal artery 10, carotid artery 12, brachial artery 14, popliteal artery 16, pedal artery 18, radial artery 20, femoral artery 22 and posterior tibial artery 24. The apical pulse is shown as 26.

The start of the arterial path is indicated by 'A' (at the exit of heart, which is the starting point of ascending aorta). A pulse may be registered in the brachial artery of the subject's left arm at the location indicated by 'B' and another pulse may be registered at location 'C' in an artery of the subject's left leg.

Based on pulses located at position 'B' and 'C', their difference in time $PD_{BC}$ can be computed. Assuming the arterial pathway lengths from 'A' to 'B' and 'A' to 'C' are known and denoted by $D_{AB}$ and $D_{AC}$, respectively, then the PWV could be estimated by $PWV=(D_{AC}-D_{AB})/PD_{BC}$, assuming that the mean PWV in both branches is the same.

The invention provides two approaches to estimate PWV. In a first approach only a pressure sensitive mattress with a 2D sensing grid is used as a sensor. In the second approach the same pressure sensitive mattress may be combined with means to capture a ballistocardiography (BCG) signal.

Figure 2:
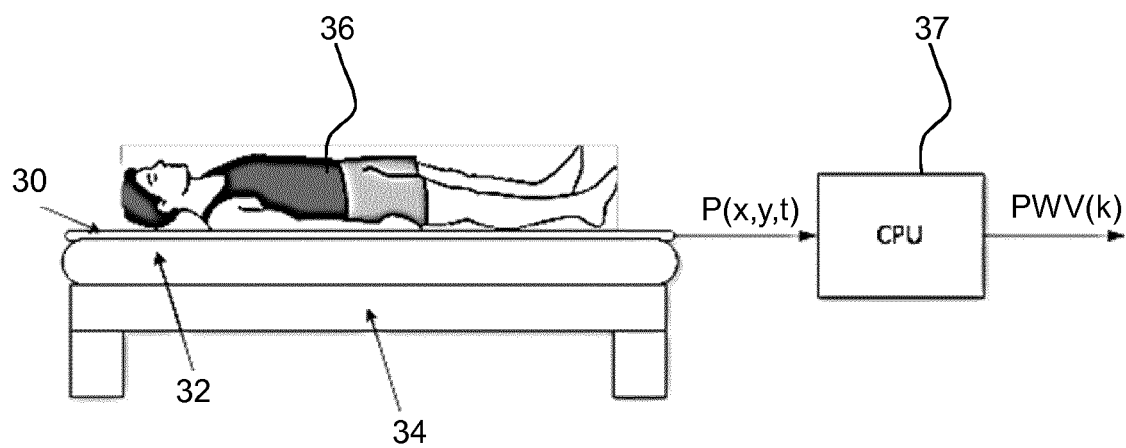
FIG. 2 shows a first example of a system for determining a pulse wave velocity.

FIG. 2 shows a first example of a system, with a pressure sensitive mat 30 provided on a mattress 32 on a bed frame 34. The pressure sensitive mat 30 lies in a single plane, although it may be deformed to match the profile of a mattress. A subject 36 is lying horizontally on the pressure sensitive mat 30. The pressure sensitive mat captures a pressure distribution profile as function of time P(x,y,t), where parameter x,y refers to the x- and y-coordinates of a 2D pressure profile and parameter t is time.

Figure 3:
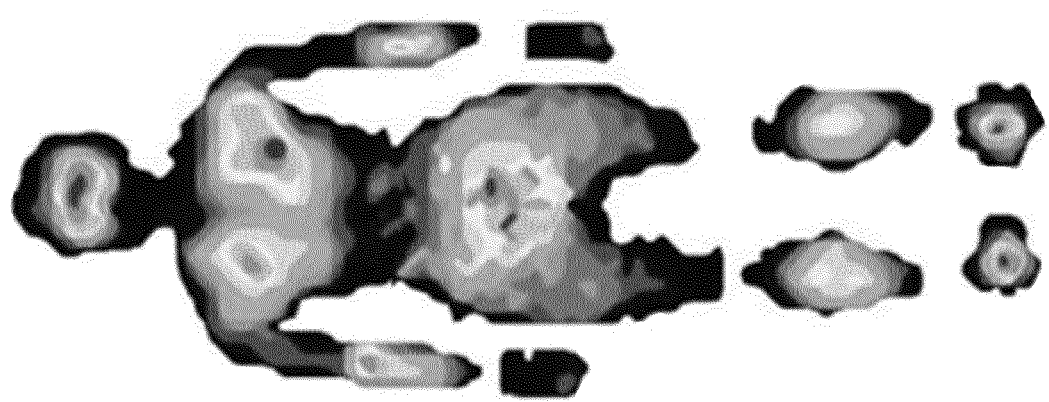
FIG. 3 depicts the spatial pressure distribution of a human lying on a pressure sensitive mat at a certain time.

As an example, FIG. 3 depicts the spatial pressure distribution of a human lying on a pressure sensitive mat at a certain time.

A controller 37 in the form of a central processing unit (CPU) receives the pressure distribution P(x,y,t) as input and runs dedicated algorithms to extract an estimate of the mean pulse wave velocity as function of time PWV(k), where k denotes a time index.

Figure 4:
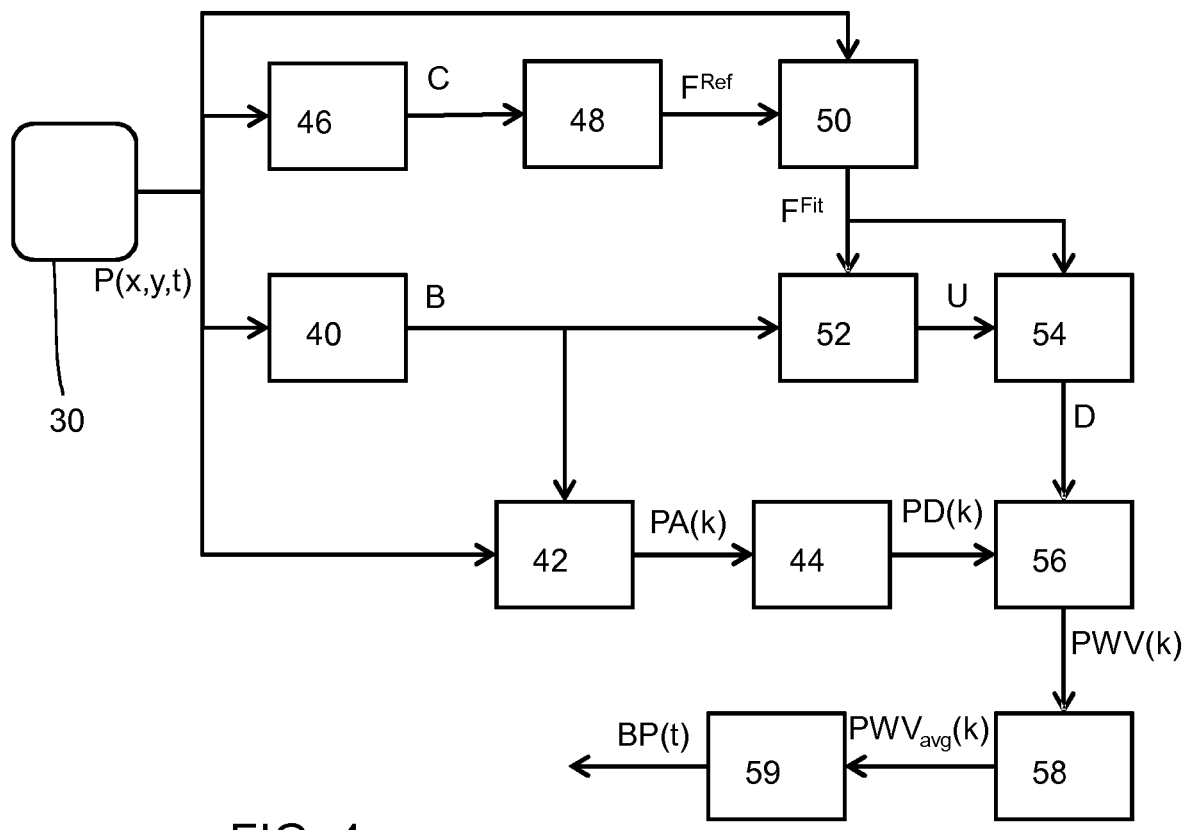
FIG. 4 shows a block diagram of the processing units used within the system of FIG. 2.

A block diagram of the processing units used to estimate PWV(k) from P(x,y,t) is illustrated in FIG. 4.

The pressure mat 30 provides the pressure distribution profile over time P(x,y,t).

A beat localization unit 40 has as input P(x,y,t) and outputs a set of N coordinates denoted by $B=\{(X_{B1},Y_{B1}), (X_{Bn},Y_{Bn}), \ldots, (X_{BN},Y_{BN})\}$ representing the extracted spatial beat locations. Localization of beats in the pressure distribution is performed by spatiotemporal analysis of pressure modulations that characterize variations in the blood volume pulse.

The set of extracted beat locations B and the original measured pressure distribution P(x,y,t) is input to a pulse arrival estimation unit 42. For each detected beat location, a local spatiotemporal analysis is performed of the pressure distribution in the spatial vicinity of the localized beat.

This is performed to determine the start and end moment of the cardiac cycle, as well as the exact moment where the blood volume pulse arrives at the beat location within the $k^{th}$ cardiac cycle.

The cardiac cycle interval and pulse arrival moment are estimated by analyzing the pressure gradient deduced from the pressure distribution signal in the neighborhood of the corresponding beat location.

The moment where the gradient reaches its maximum during the systolic phase refers to the moment the blood pulse arrived at the site that induced the registered pressure variation. For each $n^{th}$ extracted beat location and $k^{th}$ cardiac cycle a pulse arrival moment $PA_{Bn}(k)$ is determined in units of ms, giving the set PA(k).

This is an example of pulse arrival detection. Also other methods based on e.g. analyzing higher order derivatives, and wavelets, apply. Any method able to determine the onset of the pulse wave may be applied.

Figure 5:
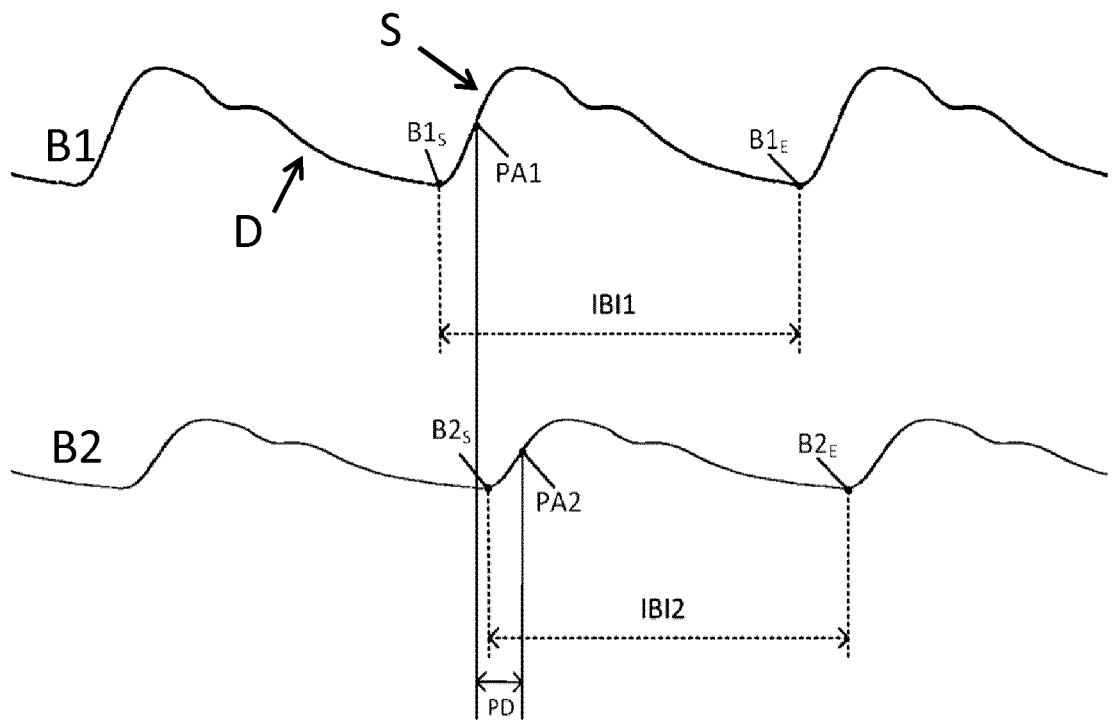
FIG. 5 is used to show how the start moment, end moment and pulse arrival detection may be performed.

FIG. 5 is used to show how the start moment, end moment and pulse arrival detection may be performed.

The trace B1 is a first pressure signal extracted by spatiotemporal analysis of the pressure signal P(x,y,t) in the local spatial vicinity of first localized beat, for example at some location on left upper arm. The pressure signal is modulated by the blood volume pulse caused by the pumping heart. The signal has a diastolic phase D and a systolic phase S.

The trace B2 is a second pressure pulse signal extracted by spatiotemporal analysis of the pressure signal P(x,y,t) in the local space vicinity of a second localized beat, for example at some location on left upper leg.

There are various strategies to localize the pulse arrival moments within a beat signal.

One approach is to slice the beat signal such that each segment represents a cardiac cycle, also known as the interbeat interval (IBI). This could be done by searching for minima marking the end of a cardiac cycle/start of next of cardiac cycle. Thus, the interbeat interval IBI1 for the first pressure signal B1 extends between a beat start $B1_S$ and a beat end $B1_E$, and the interbeat interval IBI2 for the second pressure signal B2 extends between a beat start $B2_S$ and a beat end $B2_E$.

Within an IBI segment, the pulse arrival moment is localized by analyzing the gradient of the beat signal. The moment where gradient reaches maximum value in the systolic part S refers to the pulse arrival moment. PA1 refers to the pulse arrival moment within IBI1 and PA2 refers to the pulse arrival moment within IBI2.

The pulse delay PD is the time difference between PA2 and PA1 (in units of ms).

Note that instead of localizing PA as the point where the gradient of the beat signal reaches its maximum value, the foot of the pulse $B1_S$ may serve as the pulse arrival moment. This is less preferred.

In more general terms, pulse timing information is obtained from the beat locations by analyzing the pressure signals to determine a start and end of the cardiac cycle and pulse arrival moment at that location within a given cardiac cycle. The pulse timing information thus comprises pulse arrival times.

The estimations of the pulse arrival moments PA(k) are input to a pulse delay (PD) estimation unit 44. For each possible beat location pair, a pulse delay estimate:

$$PD_{Bi,Bj}(k) = PA_{Bi}(k) - PA_{Bj}(k)$$

is computed, where i,j refers to the $i^{th}$ and $j^{th}$ extracted beat location. The unit 44 outputs for the $k^{th}$ cardiac cycle a set of pulse delay estimates:

$$PD(k) = \{PD_{Bu,Bv}(k)\}, \text{ where } u,v \in \{1 \ldots N\}, u \neq v \text{ and } PD_{Bu,Bv}(k) > 0$$

This example provides further pulse timing information in the form of a set of pulse delay estimates based on the difference between the pulse arrival moments for a set of pairs of beat locations.

The processing units 40, 42, 44 thus provide processing to obtain pulse delay estimates.

In order to derive pulse wave velocity information, the location of the pulse signals, and in particular arterial length information, is also needed.

A posture classification unit 46 (which may for example provide fitting of the posture to a reference skeleton) receives the pressure distribution P(x,y,t) and then detects the posture of the subject by means of a trained posture classifier.

The posture classification unit outputs the most probable posture C.

Classification is performed by matching the measured pressure distribution to a set of predefined reference human skeleton (or stick) models. These reference models are stored as a set 48 of reference skeleton positions.

Figure 6:
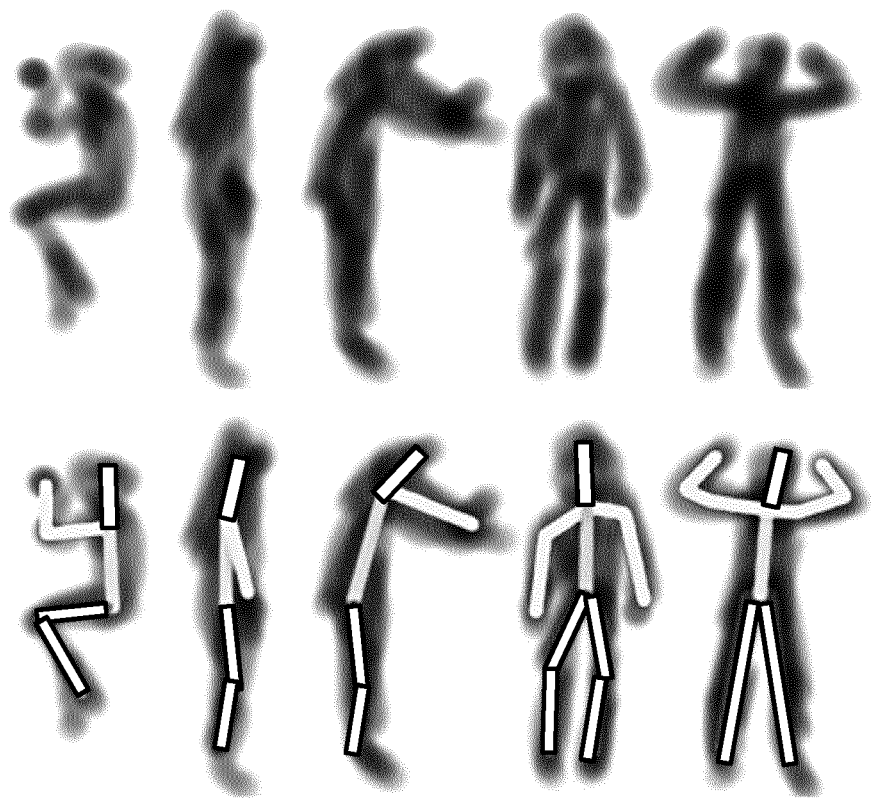
FIG. 6 shows some examples of possible pressure distributions measured for various postures.

FIG. 6 shows some examples of possible pressure distributions measured for various postures. The top set of images show the pressure distribution shapes.

Referring back to FIG. 4, a skeleton fitting unit 50 takes into account the human morphological proportions and for example involves the following steps: blob extraction/dilation, segmentation, body part detection and model fitting of the torso, head and limbs. The bottom set of images in FIG. 6 show examples of fitted skeletons $F^{Fit}$ for the different postures.

The reference model $F^{Ref}$ from the set 48 that yields the closest match is selected and fitted to the measured pressure distribution resulting in $F^{Fit}$ which is output from the skeleton fitting unit 50.

Thus, the method in this way obtains a subject posture by matching the measured pressure distribution to a set of predefined reference human form models.

A beat-skeleton mapping unit 52 is used to identify which locations on the subject's body induced the detected pressure variations in the set B that contains the extracted locations of blood volume variations in major arteries. The detected beat locations in the pressure sequence are mapped anatomically to the real locations on the human body that induced the pressure modulation, irrespective of the subject's position and posture on the pressure sensitive mat.

Detecting the location on the subject's body corresponding to a detected pressure variation is accomplished by mapping the extracted pulse locations in the set B to the fitted skeleton $F^{Fit}$ and these are the inputs to the unit 52. The set U that is output by the beat-skeleton mapping unit 52 comprises information which expresses the relationship between extracted beat locations and the fitted skeleton model $F^{Fit}$.

An arterial path length estimation unit 54 estimates, for each mapped beat location from set U, the arterial path length, i.e. the length of arterial path starting from the heart to the site on the body that induced the pressure variation. In the skeleton model, the heart is located where the torso, head and arm extremities connect each other. The heart locations are predefined in all available skeleton models.

Knowing the subject's height and the human morphologic proportions of the skeleton model's body segments, this information allows estimation of the actual arterial path length for each detected beat location that is mapped to the skeleton model.

The arterial path length estimation unit 54 outputs the set $D = \{D_{Bn}\}$ where $n = \{1 \ldots N\}$ containing for each detected beat location its estimated arterial path length.

The posture classification unit 46, the set 48, the skeleton fitting unit 50, the beat-skeleton mapping unit 52, and the arterial path length estimation unit 54 thus provide arterial path length information for each beat location.

A pulse wave velocity (PWV) estimation unit 56 has as inputs the set PD(k) containing the pulse delay estimates between each possible beat location pair during the $k^{th}$ cardiac cycle, and the set D containing for each localized beat its arterial path length. The pulse wave velocity estimation unit 56 estimates for each possible beat pair the PWV based on the arterial path distances and pulse delay associated with the beats that formed the pair. In order to compute the PWV, first the difference in arterial path length $D_{Bu,Bv}$ is calculated by subtracting the atrial path lengths derived for a given valid beat pair Bu,Bv. The pulse wave velocity estimation unit 56 outputs at each $k^{th}$ cardiac cycle a set PWV(k) containing the estimates:

$$PWV_{Bu,Bv}(k) = D_{Bu,Bv} PD_{Bu,Bv}(k)$$

for each possible valid beat pair where PD>0.

Finally, the mean of the set PWV(k) is computed in averaging unit 58, which yields the PWVavg(k) in units of m s$^{-1}$.

The value PWVavg(k) represents the average pulse wave velocity by computing the mean of PWV estimates that are obtained by combining all possible beat signals within one cardiac cycle k. Each beat signal pair gives one PWV estimate.

Note that multiple distinct beat locations could be detected with the pressure sensitive mat, e.g. at left upper arm, left lower arm and left upper leg. Each beat location yields a pressure signal (beat signal) that is modulated by variations in the blood volume pulse due to the pumping heart. When multiple beat signals can be extracted, beat signals could be combined by forming a beat pair giving one PWV estimate for each pair. For example beat signal extracted at the left upper and left lower arm yields one PWV. Also, beat signals at the left upper arm and left upper leg form a pair and results in a second PWV estimate in the same cardiac cycle. Both PWV estimates can be averaged which yields PWVavg.

As an alternative, based on a set of PWV estimates, the final PWV output by the system could be based on evaluating the quality of the extracted beat locations, beat signals, pulse arrival moments, arterial path lengths, etc.

A blood pressure measure may then be obtained (in conventional manner) from the pulse wave velocity. A blood pressure derivation unit 59 is shown which stores derived blood pressure values over time as the set BP, which comprise a set of values BP(t) at successive time points. It may use the the Moens-Korteweg equation.

The approach of FIG. 4 is based on obtaining pulse delay estimates and using these to derive a measure of pulse wave velocity.

Figure 7:
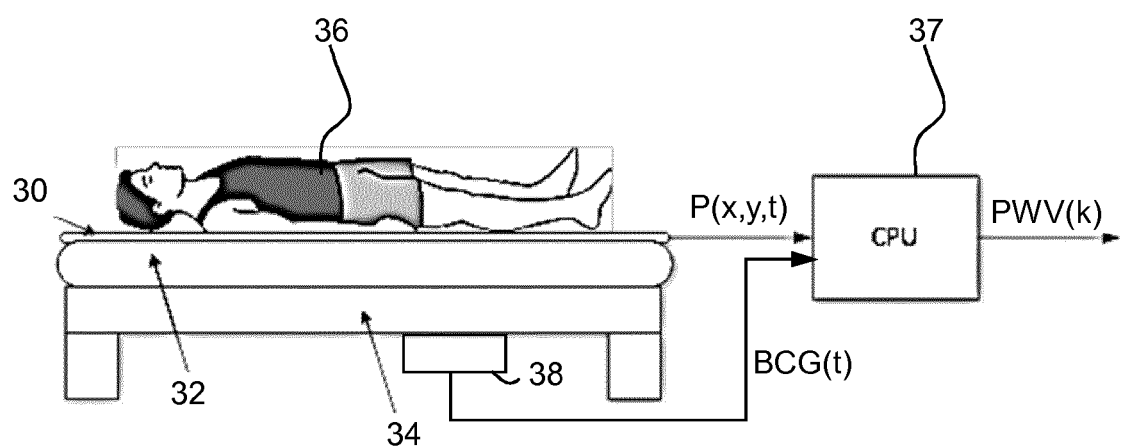
FIG. 7 shows a second example of a system for determining a pulse wave velocity.

FIG. 7 shows a second example of a system.

The same components as in FIG. 2 are given the same reference numbers. Compared to FIG. 2, the system comprises an additional acceleration sensor 38 which is used to register the ballistic forces on the subject's body. In more general terms, there is a body motion signal sensor, which may comprise accelerometers or gyroscopes or load cells. The body motion signal sensor is used to monitor the heart's activity to obtain the time of ventricular contraction, ejection or a similar measure of systole onset. Although in FIG. 7 the sensor 38 is illustrated as being mounted on the bed frame 34 underneath the mattress 32, in other examples the sensor 38 may be mounted on (or alternatively embedded in) the mattress 32 or the pressure sensitive mat 30. For example, the sensor may be an accelerometer embedded in the 2D pressure sensing mat that functions as a ballistocardiogram. The sensor 38 outputs a signal BCG(t).

The controller 37 receives as inputs both the pressure distribution information P(x,y,t) and the ballistocardiogram BCG(t). The controller again determines an estimate of the mean pulse wave velocity as function of time PWV(k).

FIG. 8 shows the processing units to estimate PWV(k) from P(x,y,t) and BCG(t).

Processing units which are identical to those in FIG. 4 are given the same reference and the description is not repeated. There are three elements which differ compared to FIG. 2, namely units 38, 70 and 72, and they are shown in bold.

In FIG. 8, there is a pulse transmit time (PTT) estimation unit 70. Thus, as in the example of FIG. 4 the pulse timing information includes pulse arrival times, but the pulse timing information further comprises pulse transit times (instead of pulse delay times).

The PTT estimation unit receives as inputs (i) the output of the pulse arrival estimation unit 42, namely the set PA(k) of pulse arrival moments $PA_{Bn}(k)$ for each $n^{th}$ extracted beat location and $k^{th}$ cardiac cycle and (ii) the output BCG(t) of the motion sensor 38. The PTT estimation unit 70 detects in the motion signal BCG(t) the principal peak J (i.e. maximum acceleration wave) in each cardiac cycle. The J-wave refers to the acceleration of the blood volume pulse in the descending and abdominal aorta, and deceleration of the blood in the ascending aorta. The time interval between the principal peak J and blood volume arrival moment at a given beat location n is denoted by $PTT_{Bn}$.

FIG. 9 shows how the pulse transit time calculations may be performed.

The trace BCG shows the ballistocardiographic signal, for example measured with an accelerometer mounted to the bed frame.

The trace B1 shows the blood volume pulse signal extracted by spatiotemporal analysis of the pressure signal P(x,y,t) in the local spatial vicinity of the localized beat (e.g. at some location on left upper arm).

As in the example of FIG. 7, the interbeat interval IBI1 is identified based on the minima marking the end of a cardiac cycle/start of next of cardiac cycle, giving the beat start $B1_S$ and beat end $B1_E$. The moment where gradient reaches maximum value in the systolic part give the pulse arrival moment PA1. As explained above, other measures may be used to determine the pulse arrival moment.

The peak J is the peak of the "J"-wave in the BCG signal. The J-wave describes the acceleration of blood in the descending and abdominal aorta, and the deceleration of blood in the ascending aorta. There are various possible procedures to localize the J-wave. One example is to search for the extreme maximal points in the BCG signal.

The pulse transit time (PTT) is defined by the pulse arrival moment PA1 during the interbeat interval IBI1 minus moment of maximum amplitude in BCG's J-wave, within the same cardiac cycle.

In this way, the timing difference between the onset of systole and the arrival of the pressure pulse in the selected pressure variation sequence is obtained.

At each $k^{th}$ cardiac cycle, the processing block estimates the PTT for all N extracted beat locations, giving the set $PTT(k)=\{PTT_{Bn}(k)\}$, where $n=\{1 \ldots N\}$ A pulse wave velocity (PWV) estimation unit 72 in this example has as inputs the set PTT(k) containing the pulse transmit time estimates and the set D containing for each localized beat its arterial path length, from the arterial path length estimation unit 54. For each $n^{th}$ beat location the PWV is computed by $PWV_{Bn}(k)=D_{Bn}/PTT_{Bn}(k)$ giving the set PWV(k).

The processing units shown in FIGS. 4 and 8 are in practice implemented in software, as software modules. They are shown as separate units only to simplify the description. In practice, the system may be implemented as a computer program which processes the pressure distribution signals (and optionally the body motion signals) in order to derive a PWV output and optionally also a blood pressure measurement output.

The outputs may be stored for retrieval at a later time, for example as a report of the blood pressure or PWV estimates during a preceding night or successive nights.

The system above makes use of a skeletal map to translate the pressure distribution pattern into an actual body position. Other pattern mapping approaches may be used. Any pattern recognition approach may be used which maps between a general body outline as detected by the pressure sensor and a map of locations of body parts. Each detected pulse may be mapped to a body location by measuring distances to known body parts within the map of locations of body parts (such as the limb joints, heart, head, etc.).

The invention provides an automated system for determining arterial path length as well as pulse pressure timing instants, so that the determination of pulse wave velocity may be fully automated. It may operate regardless of the posture of the subject, because of the posture recognition and mapping approach. There may of course be some postures where stronger pulse signals are detected than others. However, the system can monitor PWV or blood pressure signals over time (e.g. during the night) and for periods of reduced signal strength, extrapolated values may be used.

The invention avoids the need for ECG measurements, and thus provides a totally non-invasive measurement system, requiring no electrodes for contact with the subject, and no sensors that need to be worn on the body.

FIG. 10 shows a method of analyzing a pressure distribution profile of a subject lying on a mat over time.

The method comprises:

step 80 of identifying beat locations where beat pressure signals are identified;

step 82 of obtaining pulse timing information from the beat locations;

step 84 of determining a subject posture and mapping the beat locations to anatomical body locations;

step 86 of determining an arterial path length for the anatomical body locations; and step 88 of estimating a pulse wave velocity from the pulse timing information and arterial path lengths.

As explained above, the step 82 of obtaining pulse timing information is based on determining a start and end of the cardiac cycle and pulse arrival moment.

In one example, a set of pulse delay estimates is obtained based on the difference between the pulse arrival moments for a set of pairs of beat locations.

In another example, there is additional step 81 of obtaining a body motion signal in respect of the subject. The step 82 of obtaining pulse timing information then comprises obtaining a set of pulse transit times for the set of beat locations.

The step 84 of obtaining a subject posture may involve matching the measured pressure distribution to a set of predefined reference human form models.

As discussed above, a controller 37 performs the data processing. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

The invention provides a non-invasive blood pressure monitoring system which in particular may be used during sleep.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method of analyzing a pressure distribution profile (P) of a spatial distribution of pressure over time of a subject lying on a pressure mat to derive a measure of pulse wave velocity of blood in the subject, wherein the method comprises:

identifying beat locations in the subject where beat pressure signals are identified;

obtaining pulse timing information from the beat locations;

determining from the pressure distribution profile (P) a subject posture and mapping the beat locations to anatomical body locations of the subject according to that posture;

determining an arterial path length for the anatomical body locations; and estimating a pulse wave velocity from the pulse timing information and arterial path length.

2. A method as claimed in claim 1, comprising obtaining pulse timing information from the beat locations by analyzing each beat pressure signal to determine a start and end of a cardiac cycle and pulse arrival moment at each beat location within a given cardiac cycle.

3. A method as claimed in claim 2, wherein the pulse arrival moment is obtained based on detecting a pulse onset during a systolic phase.

4. A method as claimed in claim 3, comprising detecting the pulse arrival moment when a pressure gradient reaches a maximum during the systolic phase.

5. A method as claimed in claim 2, comprising obtaining the pulse arrival moment for each beat location and each cardiac cycle.

6. A method as claimed in claim 2, wherein obtaining pulse timing information comprises obtaining a set of pulse delay estimates based on a difference between pulse arrival moments for a set of pairs of beat locations.

7. A method as claimed in claim 2, further comprising receiving a body motion signal (BCG (t)) indicative of heart activity in respect of the subject, wherein obtaining pulse timing information comprises obtaining a set of pulse transit times (PTT(k)) for a set of beat locations based on the pulse arrival moments for a set of beat locations and the body motion signal.

8. A method as claimed in claim 7, comprising detecting a peak in the body motion signal and determining a time difference between a timing of a peak and a pulse arrival time for each beat location.

9. A method as claimed in claim 1, wherein obtaining a subject posture comprises matching the pressure distribution profile (P) to a set of predefined reference human form models.

10. A method as claimed in claim 9, wherein determining the arterial path length for the anatomical body locations comprises mapping the beat location to the matched human form model.

11. A method as claimed in claim 1, comprising providing an average pulse wave velocity for a processed set of cardiac cycles.

12. A method as claimed in claim 1, further comprising deriving from the pulse wave velocity one or more of:

a blood pressure measure;

a measure of arterial stiffness; and a breathing rate.

13. A computer program comprising computer program code means which is adapted, when said computer program is run on a computer, to implement the method of claim 1.

14. A monitoring system comprising:

a pressure sensitive mat for providing a pressure distribution profile (P) of a spatial distribution of pressure over time of a subject lying on the pressure sensitive mat; and a controller for analyzing the pressure distribution profile to derive a measure of pulse wave velocity of the subject, wherein the controller is adapted to perform the method as claimed in claim 1.

15. A monitoring system as claimed in claim 14, further comprising an acceleration sensor for obtaining a body motion signal (BCG(t)).

\* \* \* \* \*